(12) United States Patent
Saadat et al.

(10) Patent No.: US 7,931,661 B2
(45) Date of Patent: Apr. 26, 2011

(54) APPARATUS AND METHODS FOR PERFORMING TRANSLUMINAL GASTROINTESTINAL PROCEDURES

(75) Inventors: Vahid Saadat, Saratoga, CA (US); Ruey-Feng Peh, Sunnyvale, CA (US)

(73) Assignee: USGI Medical, Inc., San Clemente, CA (US)

( * ) Notice: Subject to any disclaimer, the term of this patent is extended or adjusted under 35 U.S.C. 154(b) by 389 days.

(21) Appl. No.: 10/918,217

(22) Filed: Aug. 11, 2004

(65) Prior Publication Data

US 2005/0277945 A1 Dec. 15, 2005

Related U.S. Application Data

(60) Provisional application No. 60/579,715, filed on Jun. 14, 2004.

(51) Int. Cl.
*A61B 17/04* (2006.01)
(52) U.S. Cl. ......... 606/144; 600/106; 128/898; 606/148
(58) Field of Classification Search .............. 606/1, 108, 606/115, 116, 153, 167, 170, 144–146, 148–150; 600/143, 148, 144, 129, 114, 115, 106; 128/898
See application file for complete search history.

(56) References Cited

U.S. PATENT DOCUMENTS

| | | | |
|---|---|---|---|
| 2,751,912 A | 6/1956 | Christoni | |
| 3,551,987 A | 1/1971 | Wilkinson | |
| 4,134,405 A | 1/1979 | Smit | |
| 4,245,624 A | 1/1981 | Komiya | |
| 4,624,265 A | 11/1986 | Grassi | |
| 4,724,840 A | 2/1988 | McVay et al. | |
| 4,841,888 A | 6/1989 | Mills et al. | |
| 5,037,433 A | 8/1991 | Wilk et al. | |
| 5,059,201 A | 10/1991 | Asnis | |
| 5,088,979 A | 2/1992 | Filipi et al. | |
| 5,174,276 A | 12/1992 | Crockard | |
| 5,222,508 A | 6/1993 | Contarini | |
| 5,222,963 A | 6/1993 | Brinkerhoff et al. | |
| 5,251,611 A * | 10/1993 | Zehel et al. .................. | 600/141 |
| 5,254,126 A | 10/1993 | Filipi et al. | |
| 5,297,536 A | 3/1994 | Wilk | |
| 5,327,914 A | 7/1994 | Shlain | |
| 5,345,949 A | 9/1994 | Shlain | |

(Continued)

FOREIGN PATENT DOCUMENTS

EP 0 480 428 A2 4/1992

(Continued)

OTHER PUBLICATIONS

Bluett et al., "Experimental Evaluation of Staple Lines in Gastric Surgery," *Arch. Surg.*, vol. 122, Jul. 1987, pp. 772-776.

(Continued)

*Primary Examiner* — John P Leubecker
*Assistant Examiner* — Victoria W Chen
(74) *Attorney, Agent, or Firm* — Charles C. Fowler; Levine Bagade Han LLP

(57) ABSTRACT

Methods and apparatus are provided for diagnosing and treating digestive or other organs (as well as other parts of the body) endoluminally and transluminally, via instruments passed into the GI tract per-orally and/or per-anally. The instruments may, for example, pass transluminally out of the stomach and/or the colon through a breach formed therein in order to conduct diagnostic or therapeutic procedures, such as gastroenterostomy.

30 Claims, 15 Drawing Sheets

U.S. PATENT DOCUMENTS

| | | | |
|---|---|---|---|
| 5,374,275 | A | 12/1994 | Bradley et al. |
| 5,382,231 | A | 1/1995 | Shlain |
| 5,395,030 | A | 3/1995 | Kuramoto et al. |
| 5,403,326 | A | 4/1995 | Harrison et al. |
| 5,403,329 | A | 4/1995 | Hinchcliffe |
| 5,431,666 | A | 7/1995 | Sauer et al. |
| 5,433,721 | A | 7/1995 | Hooven et al. |
| 5,458,131 | A | 10/1995 | Wilk |
| 5,462,561 | A | 10/1995 | Voda |
| 5,465,894 | A | 11/1995 | Clark et al. |
| 5,501,691 | A | 3/1996 | Goldrath |
| 5,507,754 | A | 4/1996 | Green et al. |
| 5,527,322 | A | 6/1996 | Klein et al. |
| 5,540,704 | A | 7/1996 | Gordon et al. |
| 5,549,621 | A | 8/1996 | Bessler et al. |
| 5,562,686 | A | 10/1996 | Sauer et al. |
| 5,562,688 | A | 10/1996 | Riza |
| 5,571,116 | A | 11/1996 | Bolanos et al. |
| 5,573,540 | A | 11/1996 | Yoon |
| 5,613,974 | A | 3/1997 | Andreas et al. |
| 5,613,975 | A | 3/1997 | Christy |
| 5,626,588 | A | 5/1997 | Sauer et al. |
| 5,632,752 | A | 5/1997 | Buelna |
| 5,634,936 | A | 6/1997 | Linden et al. |
| 5,649,941 | A * | 7/1997 | Lary ............................ 606/159 |
| 5,662,663 | A | 9/1997 | Shallman |
| 5,700,273 | A | 12/1997 | Buelna et al. |
| 5,749,893 | A | 5/1998 | Vidal et al. |
| 5,779,719 | A | 7/1998 | Klein et al. |
| 5,782,859 | A | 7/1998 | Nicholas et al. |
| 5,787,897 | A | 8/1998 | Kieturakis |
| 5,792,152 | A | 8/1998 | Klein et al. |
| 5,792,153 | A | 8/1998 | Swain et al. |
| 5,810,849 | A | 9/1998 | Kontos |
| 5,817,110 | A | 10/1998 | Kronner |
| 5,836,955 | A | 11/1998 | Buelna et al. |
| 5,860,991 | A | 1/1999 | Klein et al. |
| 5,868,762 | A | 2/1999 | Cragg et al. |
| 5,887,594 | A | 3/1999 | LoCiero, III |
| 5,897,562 | A | 4/1999 | Bolanos et al. |
| 5,901,895 | A | 5/1999 | Heaton et al. |
| 5,928,264 | A | 7/1999 | Sugarbaker et al. |
| 5,947,983 | A | 9/1999 | Solar et al. |
| 5,954,732 | A | 9/1999 | Hart et al. |
| 5,964,782 | A * | 10/1999 | Lafontaine et al. ............ 606/213 |
| 6,059,719 | A | 5/2000 | Yamamoto et al. |
| 6,086,600 | A | 7/2000 | Kortenbach |
| 6,113,609 | A | 9/2000 | Adams |
| 6,119,913 | A | 9/2000 | Adams et al. |
| 6,159,146 | A | 12/2000 | El Gazayerli |
| 6,174,323 | B1 | 1/2001 | Biggs et al. |
| 6,179,195 | B1 | 1/2001 | Adams et al. |
| 6,197,022 | B1 | 3/2001 | Baker |
| 6,231,561 | B1 | 5/2001 | Frazier et al. |
| 6,245,079 | B1 | 6/2001 | Nobles et al. |
| 6,312,437 | B1 | 11/2001 | Kortenbach |
| 6,352,503 | B1 * | 3/2002 | Matsui et al. ................. 600/104 |
| 6,358,197 | B1 | 3/2002 | Silverman et al. |
| 6,387,104 | B1 | 5/2002 | Pugsley, Jr. |
| H2037 | H | 7/2002 | Yates et al. |
| 6,494,888 | B1 | 12/2002 | Laufer et al. |
| 6,506,196 | B1 | 1/2003 | Laufer |
| 6,533,796 | B1 | 3/2003 | Sauer et al. |
| 6,537,285 | B1 | 3/2003 | Hatasaka, Jr. et al. |
| 6,543,456 | B1 * | 4/2003 | Freeman ....................... 128/898 |
| 6,554,845 | B1 | 4/2003 | Fleenor et al. |
| 6,558,400 | B2 | 5/2003 | Deem et al. |
| 6,572,629 | B2 | 6/2003 | Kalloo et al. |
| 6,584,824 | B1 | 7/2003 | Peterson |
| 6,641,592 | B1 | 11/2003 | Sauer et al. |
| 6,663,639 | B1 | 12/2003 | Laufer et al. |
| 6,695,764 | B2 | 2/2004 | Silverman et al. |
| 6,716,232 | B1 | 4/2004 | Vidal et al. |
| 6,719,763 | B2 | 4/2004 | Chung et al. |
| 6,719,764 | B1 | 4/2004 | Gellman et al. |
| 6,736,828 | B1 | 5/2004 | Adams et al. |
| 6,755,843 | B2 | 6/2004 | Chung et al. |
| 6,773,440 | B2 | 8/2004 | Gannoe et al. |
| 6,773,441 | B1 | 8/2004 | Laufer et al. |
| 6,991,602 | B2 | 1/2006 | Nakazawa et al. |
| 7,160,312 | B2 | 1/2007 | Saadat |
| 2001/0049497 | A1 | 12/2001 | Kalloo et al. |
| 2001/0049509 | A1 | 12/2001 | Sekine et al. |
| 2001/0056282 | A1 | 12/2001 | Sonnenschein et al. |
| 2002/0022851 | A1 | 2/2002 | Kalloo et al. |
| 2002/0040226 | A1 | 4/2002 | Laufer et al. |
| 2002/0055757 | A1 | 5/2002 | Torre et al. |
| 2002/0065534 | A1 | 5/2002 | Hermann et al. |
| 2002/0068945 | A1 | 6/2002 | Sixto, Jr. et al. |
| 2002/0072761 | A1 | 6/2002 | Abrams et al. |
| 2002/0078967 | A1 | 6/2002 | Sixto, Jr. et al. |
| 2002/0082621 | A1 | 6/2002 | Schurr et al. |
| 2002/0107530 | A1 | 8/2002 | Sauer et al. |
| 2002/0165589 | A1 * | 11/2002 | Imran et al. ..................... 607/40 |
| 2002/0183768 | A1 | 12/2002 | Deem et al. |
| 2002/0193816 | A1 | 12/2002 | Laufer et al. |
| 2003/0009085 | A1 | 1/2003 | Arai et al. |
| 2003/0028179 | A1 * | 2/2003 | Piskun ............................. 606/1 |
| 2003/0055442 | A1 | 3/2003 | Laufer et al. |
| 2003/0065359 | A1 * | 4/2003 | Weller et al. ................. 606/213 |
| 2003/0105476 | A1 * | 6/2003 | Sancoff et al. ................ 606/139 |
| 2003/0109892 | A1 | 6/2003 | Deem et al. |
| 2003/0139752 | A1 | 7/2003 | Pasricha et al. |
| 2003/0171651 | A1 | 9/2003 | Page et al. |
| 2003/0171760 | A1 | 9/2003 | Gambale |
| 2003/0181924 | A1 | 9/2003 | Yamamoto et al. |
| 2003/0204205 | A1 | 10/2003 | Sauer et al. |
| 2003/0208209 | A1 | 11/2003 | Gambale et al. |
| 2003/0216613 | A1 | 11/2003 | Suzuki et al. |
| 2003/0216749 | A1 | 11/2003 | Ishikawa et al. |
| 2003/0225312 | A1 | 12/2003 | Suzuki et al. |
| 2003/0229296 | A1 | 12/2003 | Ishikawa et al. |
| 2003/0236536 | A1 * | 12/2003 | Grigoryants et al. .......... 606/151 |
| 2004/0010271 | A1 | 1/2004 | Kortenbach |
| 2004/0024427 | A1 * | 2/2004 | Imran et al. ..................... 607/40 |
| 2004/0030347 | A1 | 2/2004 | Gannoe et al. |
| 2004/0049095 | A1 | 3/2004 | Goto et al. |
| 2004/0059346 | A1 | 3/2004 | Adams et al. |
| 2004/0082963 | A1 | 4/2004 | Gannoe et al. |
| 2004/0088023 | A1 * | 5/2004 | Imran et al. ..................... 607/40 |
| 2004/0092974 | A1 | 5/2004 | Gannoe et al. |
| 2004/0116949 | A1 | 6/2004 | Ewers et al. |
| 2004/0122452 | A1 | 6/2004 | Deem et al. |
| 2004/0122453 | A1 | 6/2004 | Deem et al. |
| 2004/0122456 | A1 | 6/2004 | Saadat et al. |
| 2004/0122473 | A1 | 6/2004 | Ewers et al. |
| 2004/0138529 | A1 * | 7/2004 | Wiltshire et al. .............. 600/144 |
| 2004/0138682 | A1 | 7/2004 | Onuki et al. |
| 2004/0147941 | A1 | 7/2004 | Takemoto et al. |
| 2004/0147958 | A1 | 7/2004 | Lam et al. |
| 2004/0162568 | A1 | 8/2004 | Saadat et al. |
| 2004/0167546 | A1 | 8/2004 | Saadat et al. |
| 2004/0193117 | A1 | 9/2004 | Laufer et al. |
| 2004/0193184 | A1 | 9/2004 | Laufer et al. |
| 2004/0193193 | A1 | 9/2004 | Laufer et al. |
| 2004/0193194 | A1 | 9/2004 | Laufer et al. |
| 2004/0194790 | A1 | 10/2004 | Laufer et al. |
| 2004/0220450 | A1 * | 11/2004 | Jaffe et al. ..................... 600/114 |
| 2004/0225183 | A1 * | 11/2004 | Michlitsch et al. ............ 600/106 |
| 2004/0225305 | A1 * | 11/2004 | Ewers et al. ................... 606/153 |
| 2004/0243122 | A1 * | 12/2004 | Auth et al. ....................... 606/41 |
| 2004/0249367 | A1 | 12/2004 | Saadat et al. |
| 2005/0065397 | A1 | 3/2005 | Saadat et al. |
| 2005/0065401 | A1 | 3/2005 | Saadat et al. |
| 2005/0065536 | A1 | 3/2005 | Ewers et al. |
| 2005/0075653 | A1 | 4/2005 | Saadat et al. |
| 2005/0080410 | A1 * | 4/2005 | Rioux et al. ..................... 606/41 |
| 2005/0113640 | A1 | 5/2005 | Saadat et al. |
| 2005/0119671 | A1 | 6/2005 | Reydel et al. |
| 2005/0192629 | A1 | 9/2005 | Saadat et al. |
| 2005/0203488 | A1 | 9/2005 | Michlitsch et al. |
| 2005/0203489 | A1 | 9/2005 | Saadat et al. |
| 2005/0203500 | A1 | 9/2005 | Saadat et al. |
| 2005/0216041 | A1 | 9/2005 | Okada et al. |
| 2005/0222492 | A1 | 10/2005 | Adams |
| 2005/0234294 | A1 | 10/2005 | Saadat et al. |
| 2005/0234296 | A1 | 10/2005 | Saadat et al. |

| | | | | |
|---|---|---|---|---|
| 2005/0236277 A9 * | 10/2005 | Imran et al. ............ 205/317 | WO | WO 01/85034 A1 11/2001 |
| 2005/0245945 A1 | 11/2005 | Ewers et al. | WO | WO 01/87144 A1 11/2001 |
| 2005/0247320 A1 * | 11/2005 | Stack et al. ............ 128/898 | WO | WO 01/89370 A2 11/2001 |
| 2005/0250980 A1 | 11/2005 | Swanstrom et al. | WO | WO 01/89393 A1 11/2001 |
| 2005/0250984 A1 | 11/2005 | Lam et al. | WO | WO 02/24080 A2 3/2002 |
| 2005/0250985 A1 | 11/2005 | Saadat et al. | WO | WO 02/39880 A2 5/2002 |
| 2005/0250986 A1 | 11/2005 | Rothe et al. | WO | WO 02/094105 A2 11/2002 |
| 2005/0250987 A1 | 11/2005 | Ewers et al. | WO | WO 03/007796 A2 1/2003 |
| 2005/0250988 A1 | 11/2005 | Ewers et al. | WO | WO 03/090633 A2 11/2003 |
| 2005/0251091 A1 | 11/2005 | Saadat et al. | WO | WO 03/096909 A1 11/2003 |
| 2005/0251157 A1 | 11/2005 | Saadat et al. | WO | WO 03/099137 A2 12/2003 |
| 2005/0251158 A1 | 11/2005 | Saadat et al. | WO | WO 2004/004544 A2 1/2004 |
| 2005/0251159 A1 | 11/2005 | Ewers et al. | WO | WO 2004/019787 A2 3/2004 |
| 2005/0251160 A1 | 11/2005 | Saadat et al. | WO | WO 2004/019788 A2 3/2004 |
| 2005/0251161 A1 | 11/2005 | Saadat et al. | WO | WO 2004/021865 A2 3/2004 |
| 2005/0251162 A1 | 11/2005 | Rothe et al. | WO | WO 2004/021867 A2 3/2004 |
| 2005/0251165 A1 | 11/2005 | Vaughan et al. | WO | WO 2004/021868 A2 3/2004 |
| 2005/0251166 A1 | 11/2005 | Vaughan et al. | WO | WO 2004/021873 A2 3/2004 |
| 2005/0251176 A1 | 11/2005 | Swanstrom et al. | WO | WO 2004/021894 A1 3/2004 |
| 2005/0251177 A1 | 11/2005 | Saadat et al. | WO | WO 2004/041119 5/2004 |
| 2005/0251189 A1 | 11/2005 | Saadat et al. | WO | WO 2004/064600 8/2004 |
| 2005/0251202 A1 | 11/2005 | Ewers et al. | WO | WO 2004/103430 12/2004 |
| 2005/0251205 A1 | 11/2005 | Ewers et al. | WO | WO 2004/110285 A1 12/2004 |
| 2005/0251206 A1 | 11/2005 | Maahs et al. | WO | WO 2005/011463 2/2005 |
| 2005/0251207 A1 | 11/2005 | Flores et al. | WO | WO 2005/011519 2/2005 |
| 2005/0251208 A1 | 11/2005 | Elmer et al. | WO | WO 2005/037152 A1 4/2005 |
| 2005/0251209 A1 | 11/2005 | Saadat et al. | WO | WO 2005/048815 A3 6/2005 |
| 2005/0251210 A1 | 11/2005 | Westra et al. | WO | WO 2005/050971 A2 6/2005 |
| 2005/0267523 A1 | 12/2005 | Devellian et al. | WO | WO 2005/058239 6/2005 |
| 2005/0272977 A1 | 12/2005 | Saadat et al. | WO | WO 2005/086945 9/2005 |
| 2005/0277945 A1 | 12/2005 | Saadat et al. | WO | WO 2005/104927 11/2005 |
| 2005/0277966 A1 | 12/2005 | Ewers et al. | WO | WO 2005/110244 11/2005 |
| 2005/0277975 A1 | 12/2005 | Saadat et al. | WO | WO 2005/122914 12/2005 |
| 2005/0277981 A1 | 12/2005 | Maahs et al. | WO | WO 2005/122915 12/2005 |
| 2005/0277983 A1 | 12/2005 | Saadat et al. | WO | WO 2006/019868 2/2006 |
| 2006/0009789 A1 | 1/2006 | Gambale et al. | WO | WO 2006/039199 4/2006 |
| 2006/0020274 A1 | 1/2006 | Ewers et al. | WO | WO 2006/039223 4/2006 |
| 2006/0020276 A1 | 1/2006 | Saadat et al. | WO | WO 2006/039296 4/2006 |
| 2006/0100579 A1 | 5/2006 | Maahs et al. | WO | WO 2006/078429 7/2006 |
| 2006/0135971 A1 | 6/2006 | Swanstrom et al. | WO | WO 2006/089217 8/2006 |
| 2006/0157067 A1 | 7/2006 | Saadat et al. | WO | WO 2006/093975 9/2006 |
| 2006/0161185 A1 | 7/2006 | Saadat et al. | WO | WO 2006/110275 10/2006 |
| 2006/0178560 A1 | 8/2006 | Saadat et al. | WO | WO 2006/127306 11/2006 |
| 2006/0178562 A1 | 8/2006 | Saadat et al. | WO | WO 2007/009021 1/2007 |
| 2006/0183975 A1 | 8/2006 | Saadat et al. | | |
| 2006/0184161 A1 | 8/2006 | Maahs et al. | | |
| 2006/0189845 A1 | 8/2006 | Maahs et al. | | |
| 2006/0217762 A1 | 9/2006 | Maahs et al. | | |
| 2006/0237022 A1 | 10/2006 | Chen et al. | | |
| 2006/0237023 A1 | 10/2006 | Cox et al. | | |
| 2006/0258909 A1 | 11/2006 | Saadat et al. | | |
| 2006/0271073 A1 | 11/2006 | Lam et al. | | |
| 2006/0271074 A1 | 11/2006 | Ewers et al. | | |
| 2006/0271101 A1 | 11/2006 | Saadat et al. | | |
| 2007/0123840 A1 | 5/2007 | Cox | | |
| 2007/0142849 A1 | 6/2007 | Ewers et al. | | |

FOREIGN PATENT DOCUMENTS

| | | |
|---|---|---|
| EP | 1699366 | 9/2006 |
| EP | 1804680 | 7/2007 |
| EP | 1804683 | 7/2007 |
| FR | 2 768 324 A1 | 3/1999 |
| GB | 2 165 559 A | 4/1986 |
| JP | 2007-513717 | 5/2007 |
| WO | WO 92/04870 A1 | 4/1992 |
| WO | WO 95/25468 A1 | 9/1995 |
| WO | WO 99/22649 A2 | 5/1999 |
| WO | WO 00/78227 A1 | 12/2000 |
| WO | WO 00/78229 A1 | 12/2000 |
| WO | WO 01/66018 A1 | 9/2001 |
| WO | WO 01/74260 A1 | 10/2001 |

OTHER PUBLICATIONS

Brolin et al., Experimental Evaluation of Techniques of Gastric Paritioning for Morbid Obesity, *Surgery, Gynecology & Obstetrics*, vol. 153, Dec. 1981, pp. 878-882.

Johnston et al. "The Magenstrasse and Mill Operation of Morbid Obesity", *Obesity Surgery* 13, 2003, pp. 10-16.

Okudaira et al., "The Healing and Tensile Strength of the Gastroplasty Staple Line," *American Surgeon*, Oct. 1984, pp. 564-568.

File History for U.S. Appl. No. 11/550,739, filed Oct. 18, 2006 in the name of Cox.

File History for U.S. Appl. No. 11/270,195, filed Nov. 8, 2005 in the name of Cox et al.

File History for U.S. Appl. No. 11/238,279, filed Sep. 28, 2005 in the name of Chen et al.

PCT International Patent Application No. PCT/US2005/019694 filed Jun. 3, 2005 in the name of Saadat et al, International Search Report mailed Jul. 21, 2007.

PCT International Patent Application No. PCT/US2005/019694 filed Jun. 3, 2005 in the name of Saadat et al, International Preliminary Report on Patentability mailed Jul. 10, 2007.

* cited by examiner

3 Balloons

Double Balloons

Baskets

Single Balloon

APPARATUS AND METHODS FOR PERFORMING TRANSLUMINAL GASTROINTESTINAL PROCEDURES

CROSS-REFERENCES TO RELATED APPLICATIONS

This application claims benefit from the filing date of U.S. provisional patent application Ser. No. 60/579,715, filed Jun. 14, 2004, which is incorporated herein by reference in its entirety.

BACKGROUND OF THE INVENTION

Field of the Invention

The present invention relates to apparatus and methods for endoluminal, transluminal procedures, including per-oral, transgastric and/or per-anal, transcolonic procedures. More particularly, the present invention relates to methods and apparatus for performing therapeutic and/or diagnostic procedures on various digestive or other organs or body regions, conducted via instruments inserted endoluminally and transgastrically/transcolonically.

In an effort to reduce the invasiveness of treatments for gastrointestinal ("GI") disorders, gastroenterologists, GI surgeons and others are pursuing minimally inivasive endoluminal treatments for such disorders. Treatments through natural GI passageways are being pursued utilizing instruments advanced per-orally and/or per-anally. See, for example, Applicant's co-pending U.S. patent application Ser. No. 10/734,547, filed Dec. 12, 2003, which is incorporated herein by reference in its entirety.

In view of advances in methods and apparatus for minimally invasive endoluminal GI treatment, it would be desirable to provide methods and apparatus for diagnostic or therapeutic treatment of organs of the digestive system or other parts of the body via instruments advanced per-orally and transgastrically and/or per-anally and transcolonically, or a combination thereof. Transgastric procedures from the interior of the stomach to the exterior have been described previously in U.S. patent application Publication No. 2003/0216613 (application Ser. No. 10/390,443, filed Mar. 17, 2003) to Suzuki et al. However, while that reference discusses curvable overtubes that may be maintained in a curve, it does not describe an overtube or guide that may be shape-locked or rigidized along its length.

BRIEF SUMMARY OF THE INVENTION

Methods and apparatus are provided for accessing digestive or other organs (as well as other parts of the body) endoluminally and transluminally via instruments passed into the GI tract per-orally and/or per-anally. The instruments may, for example, pass transluminally out of the stomach or the colon for performing diagnostic or therapeutic surgical procedures.

In one aspect of the invention, apparatus comprising a flexible, rigidizable overtube is provided that may be inserted per-orally or per-anally within the lumen of a patient's GI tract. The overtube preferably is flexible, rigidizable and maneuverable to allow other tools or devices to be inserted through the overtube body. A proximal region of the overtube may serve as a per-oral access platform from, e.g., the mouth to the esophageal, gastric or intestinal lumen. Alternatively, the proximal region may provide a per-anal access platform from, e.g., the rectum to the colon. A distal region of the overtube optionally may be configured to breach the GI lumen from the interior to the exterior and/or to secure against a wall of the lumen, e.g., to facilitate transluminal passage of tools or devices out of the lumen. When the distal region reversibly secures the overtube to the wall of the GI lumen in the vicinity of the luminal breach, a lumen of the overtube may be aligned with the luminal breach.

As will be apparent, the distal region optionally may be provided as a separate instrument utilized in conjunction with the overtube. Furthermore, the distal region may simply secure the overtube to the wall of the GI lumen without puncturing or breaching the lumen. In such a configuration, the GI lumen optionally may be breached by additional apparatus used in conjunction with the overtube and distal region, such as a guide or tool described hereinafter. As yet another option, the overtube may not be secured to the wall of the GI lumen at all; rather, the overtube may pass transluminally therethrough.

The apparatus optionally also may comprise a guide advanceable through the lumen of the overtube, past the distal region, and transluminally out of the GI tract from the interior to the exterior of the GI lumen. Diagnostic and/or therapeutic tools or instruments may be advanced through or along the guide for diagnostic purposes or for performing various therapeutic surgical procedures. The tools/instruments alternatively may be advanced transluminally directly through the overtube without use of an intermediary guide. As yet another alternative, the overtube may be advanced transluminally out of the GI lumen and may serve as a guide for the tools/instruments.

Once the guide has been advanced within the lumen of the overtube and passed transluminally, e.g., out of the stomach or the colon, the guide may provide an access platform for transluminal insertion of tools, instruments, devices, etc., through the overtube body to target organs or other areas of interest in the patient's body external to the GI lumen. The guide optionally may comprise articulating arms that facilitate maneuvering around obstacles.

The tools and instruments advanced through the guide provide means for diagnosing and/or performing functions on tissue at regions of interest within the patient's body. These functions include, but are not limited to, visualizing, characterizing, sampling, grasping, maneuvering, folding, piercing, suturing, approximating, and securing tissue. Additional functions, such as performing gastroenterostomy, will be apparent.

Methods of using the apparatus are also provided.

DETAILED DESCRIPTION OF THE INVENTION

The present invention relates to apparatus and methods for endoluminal, transluminal procedures, including per-oral, transgastric and/or per-anal, transcolonic procedures. More particularly, the present invention relates to methods and apparatus for performing therapeutic and/or diagnostic procedures on various digestive or other organs or body regions, conducted via instruments inserted endoluminally and transgastrically/transcolonically.

Figure 1:
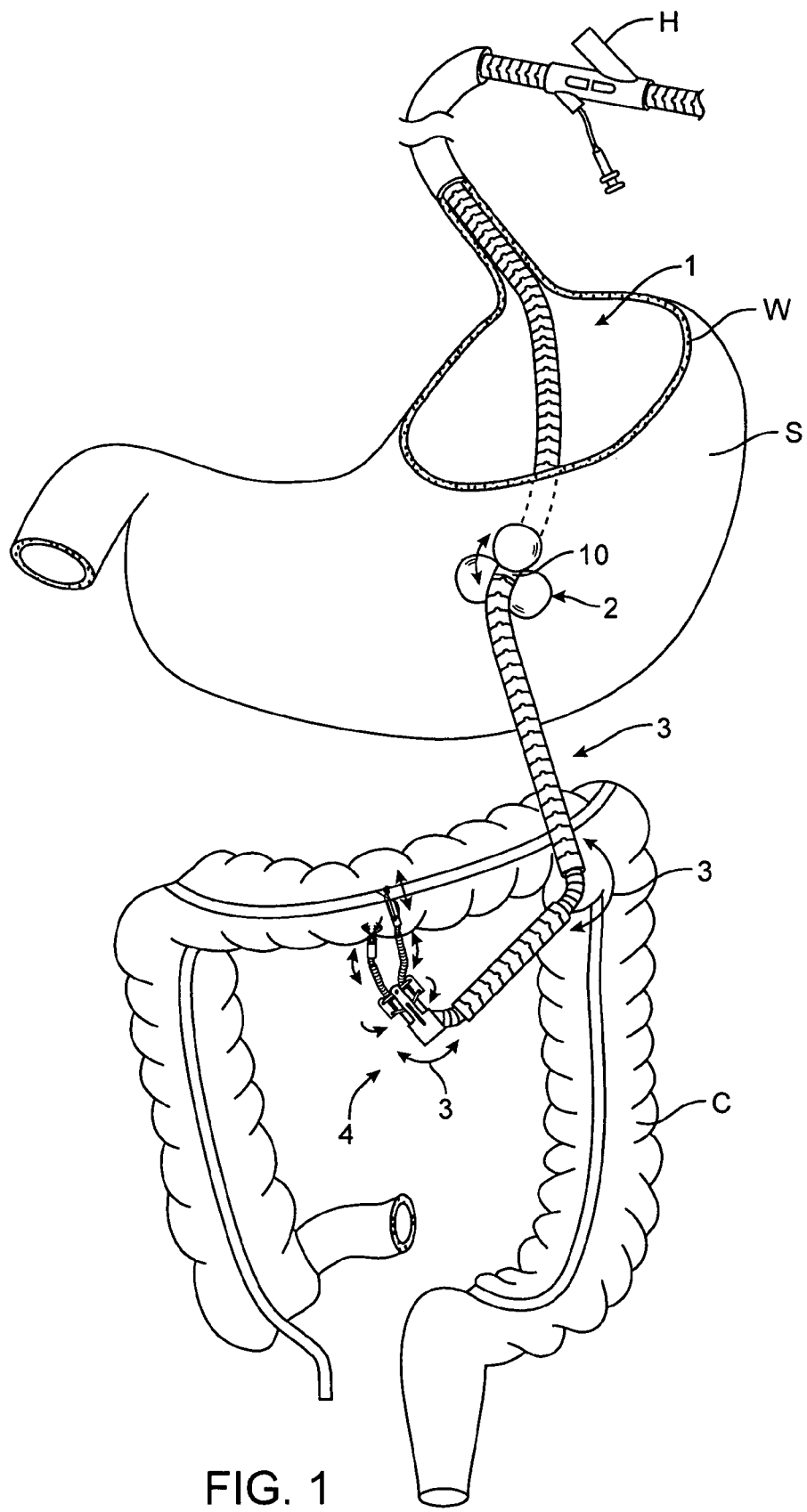
FIG. 1 is a schematic view, partially in section, of apparatus of the invention, illustrating a method of using the apparatus to conduct a per-oral, transgastric procedure.
Figure 2:
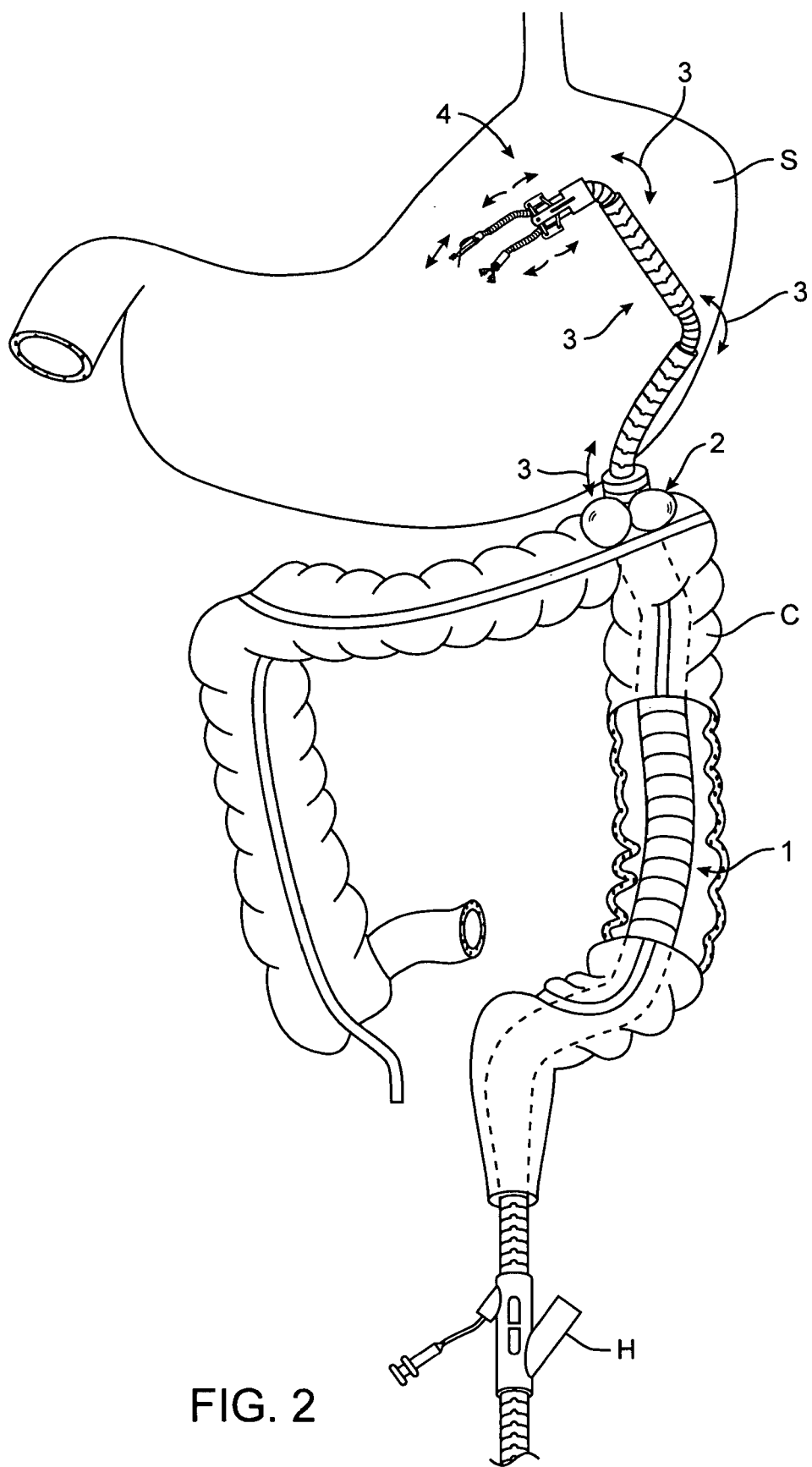
FIG. 2 is a schematic view, partially in section, of apparatus of the invention, illustrating a method of using the apparatus to conduct a per-anal, transcolonic procedure.

With reference to FIGS. 1 and 2, overtube 1 comprises a flexible, maneuverable and shape lockable conduit that may be inserted transorally, as in FIG. 1, or transanally, as in FIG. 2, into a patient's gastrointestinal ("GI") lumen. The overtube may, for example, comprise a column of coacting links that may be compressed, e.g., via pull wires extending therethrough, to steer or shape-lock/rigidize the overtube in a desired configuration. Steering may, for example, be accomplished by compressing or shortening a distance between adjacent links in a non-symmetrical fashion to induce localized steering moments. Shape-locking or rigidizing may, for example, be achieved through symmetrical compression. Handle H may facilitate such steering and/or shape-locking. Methods and apparatus for steering and shape-locking of overtube 1 are described in more detail, for example, in Applicant's co-pending U.S. patent application Ser. No. 10/797, 485, filed Mar. 9, 2004, which is incorporated herein by reference in its entirety.

In FIG. 1, the overtube is advanced into the patient's stomach S, while in FIG. 2, the overtube is advanced into the patient's colon C. Overtube 1 comprises distal region 2, which optionally may be configured to breach, pierce, etc., the GI lumen for passage of instruments transluminally from the interior of the lumen to the exterior, e.g., from the interior of the stomach or colon to the exterior of the stomach or colon. Distal region 2 also optionally may be configured to attach to the wall of the GI lumen to act as a conduit for passage of instruments across the wall. As yet another option, the distal region may be advanced transluminally out of the GI lumen.

In FIGS. 1 and 2, the distal region illustratively comprises one or more balloons for reversibly securing the distal region to the wall of the GI lumen at the location where the lumen is breached. Additional and alternative distal regions are described hereinafter with respect to FIGS. 3 and 4. As will be apparent to those of skill in the art, distal region 2 optionally may be provided as a separate instrument used in conjunction with overtube 1.

As seen in FIGS. 1 and 2, overtube 1 also comprises a lumen through which guide 3 has been advanced transluminally out of the patient's GI tract. Overtube 1 preferable has been rigidized, e.g., via actuation of handle H, prior to advancement of guide 3 therethrough. Guide 3 preferably comprises a flexible, shape-lockable, steerable and/or articulating conduit that can be inserted through overtube 1 and then extended to access different areas of the body once it has exited the GI lumen, e.g., once it has exited the patient's stomach or colon. It is expected that the guide's flexible, shape-lockable, steerable and/or articulating properties will enable the guide to access many desired locations within the body by negotiating obstructions during advancement. Furthermore, guide 3 (as well as overtube 1) may comprise multiple sections that are configured to articulate relative to one another to enhance maneuverability of the guide, as well as of tools 4 advanced therethrough. Multi-sectioned, steerable and/or shape-lockable guides are described, for example, in greater detail in Applicant's aforementioned U.S. patent application Ser. No. 10/797,485, filed Mar. 9, 2004, which has been incorporated herein by reference.

As described hereinafter with respect to FIG. 5, a distal end of guide 3 preferably comprises a visualization element, such as a camera or visual sensor, configured to transmit images to an external monitor. Furthermore, guide 3 preferably comprises multiple lumens for delivering and deploying tools or instruments 4 at target sites external to the GI lumen in order to perform desired diagnostic or therapeutic functions. The visualization element and/or one or more lumens of guide 3 may be able to articulate relative to other portions of the guide. For example, the visualization element or the lumens may be able to articulate away from the longitudinal axis of the guide.

As seen in FIGS. 1 and 2, tools or instruments 4 may be advanced through guide 3 to the exterior of the patient's GI tract. Guide 3 preferably is steered to a desired location and rigidized or shape-locked before advancement of tools 4. As will be apparent, instruments 4 alternatively may be advanced concurrently with guide 3, while guide 3 is not shape-locked, and/or directly through overtube 1 without use of guide 3. Tools 4 may articulate and/or extend and retract relative to guide 3. As shown, tools 4 illustratively comprise visualization, grasping, maneuvering, piercing, folding, approximating and securing elements. However, additional functions may be achieved utilizing tools advanced through or coupled to overtube 1/guide 3, including, but not limited to, characterizing, sampling and suturing tissue. Additional functions will be apparent. An illustrative distal end of guide 3 and an illustrative set of tools 4 are described in greater detail hereinafter with respect to FIG. 5.

Referring now to FIG. 3, embodiments of distal region 2 of overtube 1 are described. In FIG. 3A, distal region 2 is shown positioned across the wall of stomach S, such that overtube 1 acts as a conduit passing through the wall. Guide 3 is positioned through the lumen of overtube 1, such that the guide passes transgastrically out of the GI lumen. Distal region 2 of overtube 1 may comprise a piercing element, such as a sharpened circumferential end of overtube 1, for breaching the wall of the GI lumen. Additional piercing elements will be apparent.

Figure 3C:
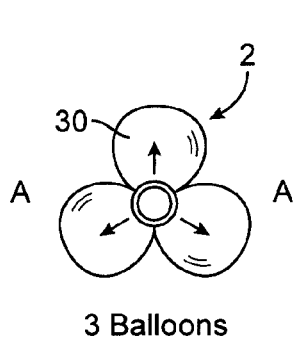
FIGS. 3A-3E are, respectively, a schematic view, partially in section, of an overtube of the apparatus, illustrating reversible attachment of the overtube to a wall of the patient's GI lumen in a vicinity of a transluminal breach of the wall, and detail views of exemplary distal regions for use with the overtube to secure the overtube to the wall of the lumen.
Figure 3A:
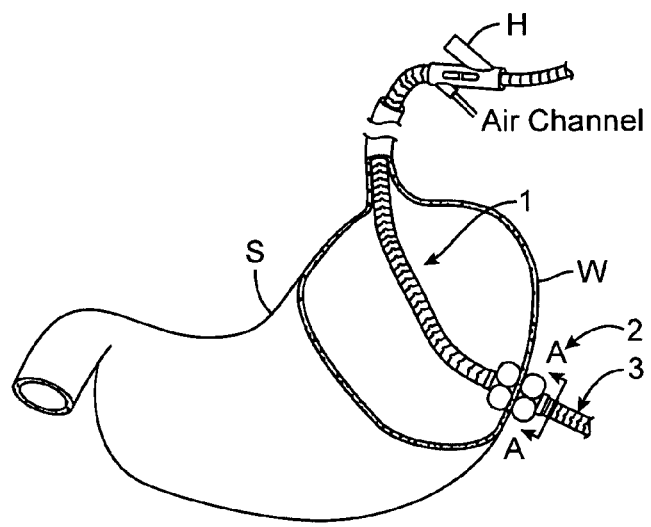
Figure 3B:
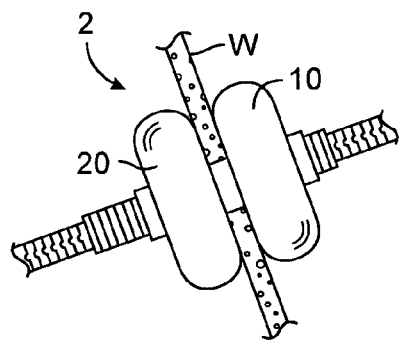

In FIG. 3B, distal region 2 illustratively comprises first balloon member 10 and second balloon member 20 that reversibly secure overtube 1 against wall W of the GI lumen at the location where the overtube crosses the lumen. When properly positioned, the first and second balloon members may be inflated to secure the overtube, and may be deflated for repositioning or removal of the overtube. In use, distal region 2 may be secured against wall W prior to passage of guide 3 through the overtube. Alternatively, second balloon member 20 may be inflated, guide 3 may be passed through the overtube and across the wall, and then overtube 1 may be advanced, such that second balloon member 20 engages the wall and first balloon member 10 is disposed exterior to the GI lumen. Balloon member 10 then may be inflated to engage the exterior of wall W and secure the overtube relative to the wall by capturing the wall between the first and second balloon members. In such a configuration, guide 3 may comprise the piercing element for piercing or breaching wall W.

Inflatable members 10 and 20 optionally may comprise multiple balloon members, such as triple balloon members 30 of FIG. 3C, which may be utilized in a similar fashion to the unitary balloon members of FIG. 3B. Triple balloon members 30 optionally may be inflated individually or to varying degrees, for example, to articulate or otherwise orient distal region 2 of overtube 1. Alternatively, a single balloon member 40 may be used in place of separate balloon members 10 and 20, as seen in FIG. 3D. Member 40 preferably may be passed across GI tissue wall W in a collapsed, deflated configuration, and then inflated to secure overtube 1 to the wall. Furthermore, when distal region 2 is provided as a separate device used in conjunction with overtube 1, member 40 may be utilized to dilate the opening across wall W to facilitate passage of overtube 1 therethrough.

Figure 3E:
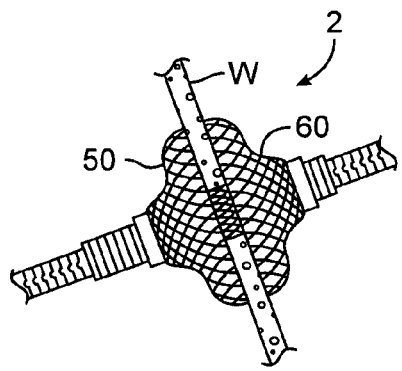
Figure 3D:
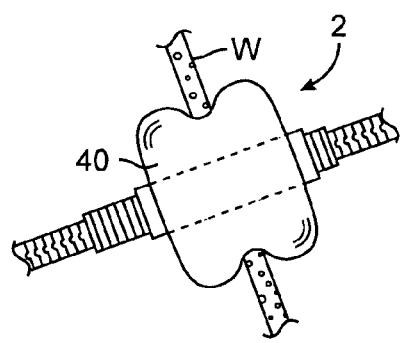
Figure 4A:
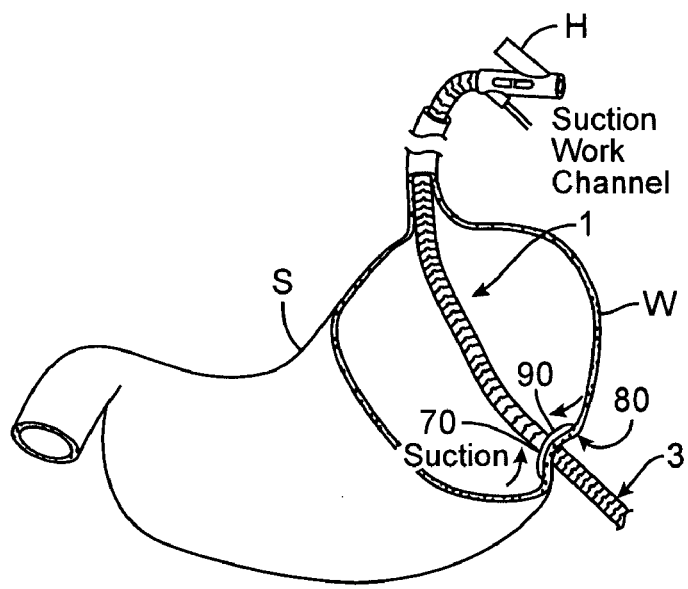
FIGS. 4A-4E are, respectively, a schematic view, partially in section, of an overtube having a distal region that reversibly attaches to the wall of the GI lumen without puncturing the lumen, and detail views of alternative distal regions for securing the overtube to the wall of the lumen.
Figure 4C:
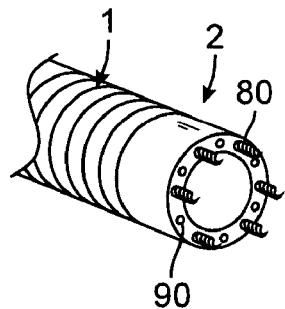
Figure 4B:
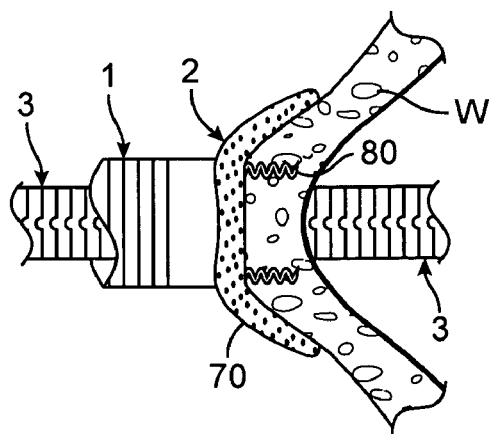
Figure 4D:
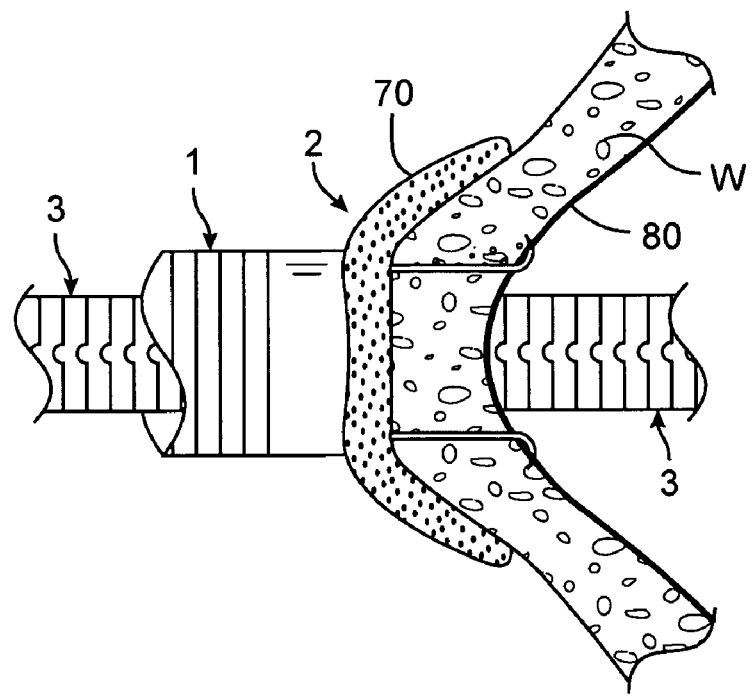
Figure 4E:
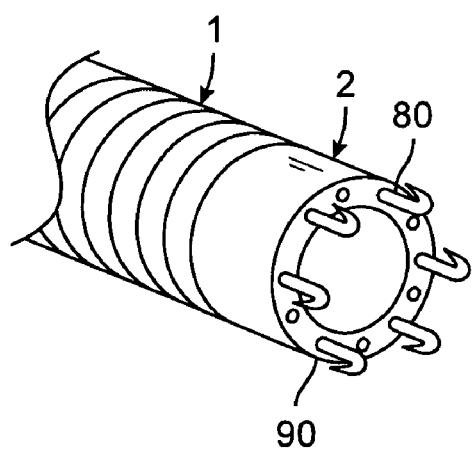

As seen in FIG. 3E, instead of utilizing inflatable members 10 and 20, first and second basket members 50 and 60 may be provided. Basket members 50 and 60 preferably are flexible and expandable baskets with shape memory properties. Expanding and deploying members 50 and 60 in a securing configuration similar to the securing configuration of balloon members 10 and 20 reversibly attaches distal region 2 of overtube 1 to wall W of the GI lumen.

Referring now to FIG. 4, an alternative embodiment of distal region 2 of overtube 1 is shown. In FIG. 4A, distal region 2 is shown engaging wall W of stomach S, with guide 3 passing through overtube 1 and exiting the gastric lumen. As seen in FIGS. 4B-4E, distal region 2 illustratively comprises seal member 70, tissue grasper members 80 and suction lumen members 90. Suction lumen members 90 preferably are distributed about the circumference of distal region 2, as shown in FIGS. 4C and 4E. In use, distal region 2 may engage wall W by drawing suction through suction lumen members 90, deploying seal member 70, and securing the engaged tissue with tissue grasper members 80. FIG. 4B shows a plane detail view, partially in section, of a helix screw version of tissue grasper members 80. FIG. 4C shows a perspective detail view of the helix members, which may rotate in a coordinated manner at the tip of distal region 2. Tissue grasper members 80 alternatively may comprise hook members, as shown in FIGS. 4D and 4E.

Figure 5:
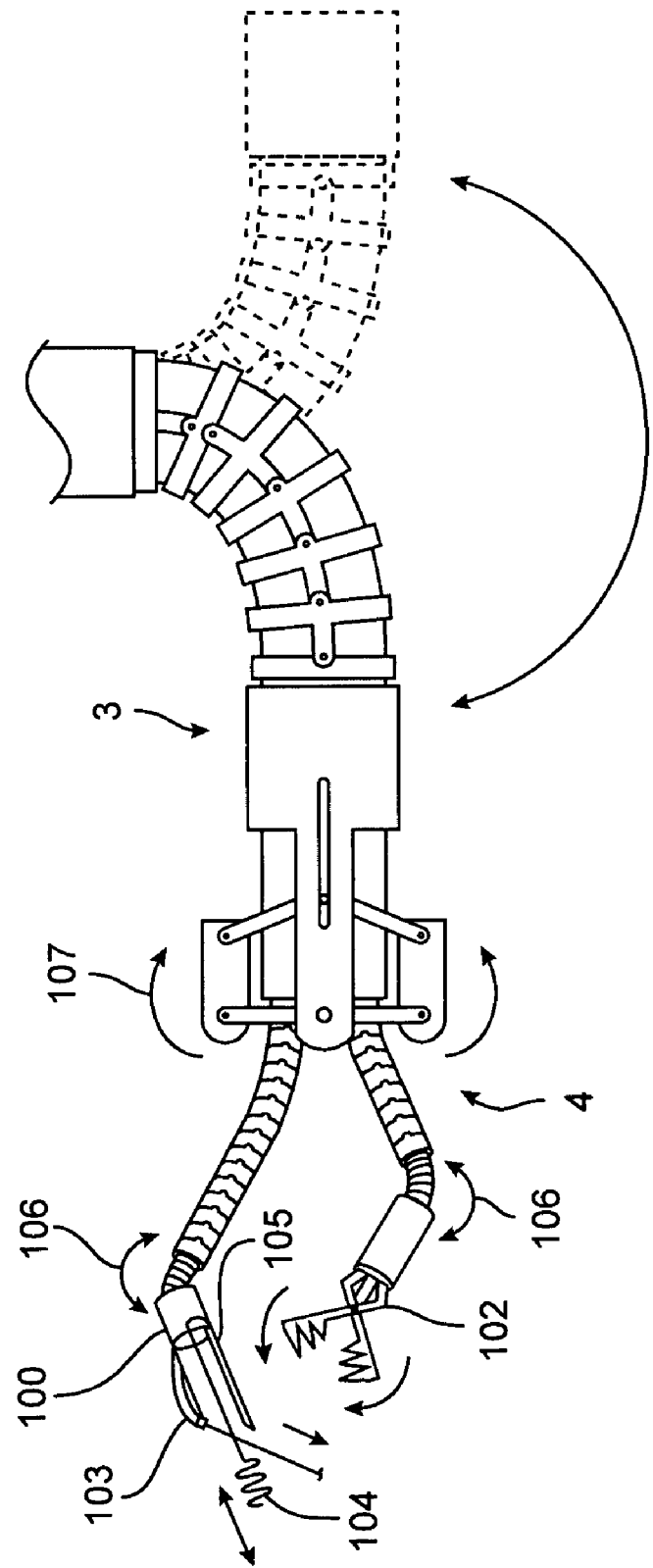
FIG. 5 is a detail plan view of a guide and instruments advanceable through the guide, illustrating articulation of the guide and the instruments to facilitate diagnostic and/or therapeutic transluminal procedures.

With reference now to FIG. 5, a distal region of an illustrative guide 3 and set of tools 4 are described. Instruments or tools 4 may comprise, for example, plicator arm member 100 configured to, e.g., grasp, pierce, manipulate, approximate and secure target tissue. Tools 4 also may comprise second arm member 102, which may, for example, be used in conjunction with plicator arm member 100 for grasping, maneuvering and pulling of target tissue, etc. Plicator arm member 100 illustratively comprises needle sub-member 103, which is used to position and pierce tissue. Plicator member 100 further comprises helix sub-member 104, which is deployable forwards and backwards to grab and hold tissue. Complementary to this is bail sub-member 105 on plicator member 100 that serves the function of approximating and/or folding tissue after tissue is engaged, e.g., via helix sub-member 104. Both plicator arm 100 and second arm member 102 comprise articulating sub-member 106 for maneuvering the arms.

Camera member 107 is an articulating visualization element for capturing live images of the area on which tools 4 are operating. The camera member illustratively is provided on the distal end of guide 3. Camera member 107 may be deployed by articulating the member off-axis from the longitudinal axis of guide 3. This may also serve to expose the distal opening(s) of lumen(s) within guide 3 to allow advancement of instruments 4 distal to the guide. Articulating visualization elements, as well as articulating lumens and tools, are described, for example, in Applicant's co-pending U.S. patent application Ser. No. 10/824,936, filed Apr. 14, 2004, which is incorporated herein by reference in its entirety.

Referring again to FIG. 1, an illustrative method for performing a per-oral, transgastric surgical procedure is described. As seen in FIG. 1, overtube 1 is advanced through a patient's mouth, down the patient's throat, into the patient's stomach S. The wall of stomach S is then pierced to allow for transluminal passage of instruments out of the patient's stomach. The wall may be pierced, for example, via distal region 2 of overtube 1, via guide 3, via a tool 4 comprising a piercing element, or by any other known technique. Distal region 2 of overtube 1 is secured against the wall of stomach S, e.g., at the location of breach, such that the lumen of the overtube provides a conduit for passage of instruments across the wall of the stomach. Guide 3 optionally may be advanced through the lumen of overtube 1 to facilitate proper positioning of instruments 4 for conducting a diagnostic or therapeutic procedure external to the GI lumen. The instruments then may be advanced through the guide, and a per-oral to endoluminal to transgastric procedure may be performed. Overtube 1 preferably is shape-locked or rigidized prior to, during, or after advancement of guide 3 or tools 4 therethrough. Likewise, guide 3 preferably is shape-locked or rigidized prior to, during, or after advancement of tools 4 therethrough. In FIG. 1, a procedure illustratively is conducted on the patient's colon C. Additional procedures will be apparent.

Referring again to FIG. 2, an illustrative method for performing a per-anal, transcolonic surgical procedure is described. As seen in FIG. 2, overtube 1 is advanced through a patient's anus into the patient's colon C. The wall of the colon is then pierced to allow for transluminal passage of instruments out of the patient's colon. The wall may be pierced, for example, via distal region 2 of overtube 1, via guide 3, via a tool 4 comprising a piercing element, or by any other known technique. Distal region 2 of overtube 1 is secured against the wall of colon C at the location of breach, such that the lumen of the overtube provides a conduit for passage of instruments across the wall of the colon. Guide 3 optionally may be advanced through the lumen of overtube 1 to facilitate proper positioning of instruments 4 for conducting a diagnostic or therapeutic procedure external to the GI lumen. The instruments then may be advanced through the guide, and a per-anal to endoluminal to transcolonic procedure may be performed. Overtube 1 preferably is shape-locked or rigidized prior to, during, or after advancement of guide 3 or tools 4 therethrough. Likewise, guide 3 preferably is shape-locked or rigidized prior to, during, or after advancement of tools 4 therethrough. In FIG. 2, a procedure illustratively is conducted on the patient's stomach S. Additional procedures will be apparent.

Referring now to FIG. 6, an illustrative method of performing per-oral, transgastric gastroenterostomy is described. In FIG. 6A, overtube 1 has been advanced per-orally into the patient's stomach S. Distal region 2, which illustratively comprises a separate tubular member that has been advanced over overtube 1, is secured to wall W of the stomach via first and second balloon members 10 and 20, respectively. Wall W has been breached for transluminal passage of instruments therethrough. Overtube 1 has been steered and advanced to the exterior of the stomach through distal region 2.

Figure 6A:
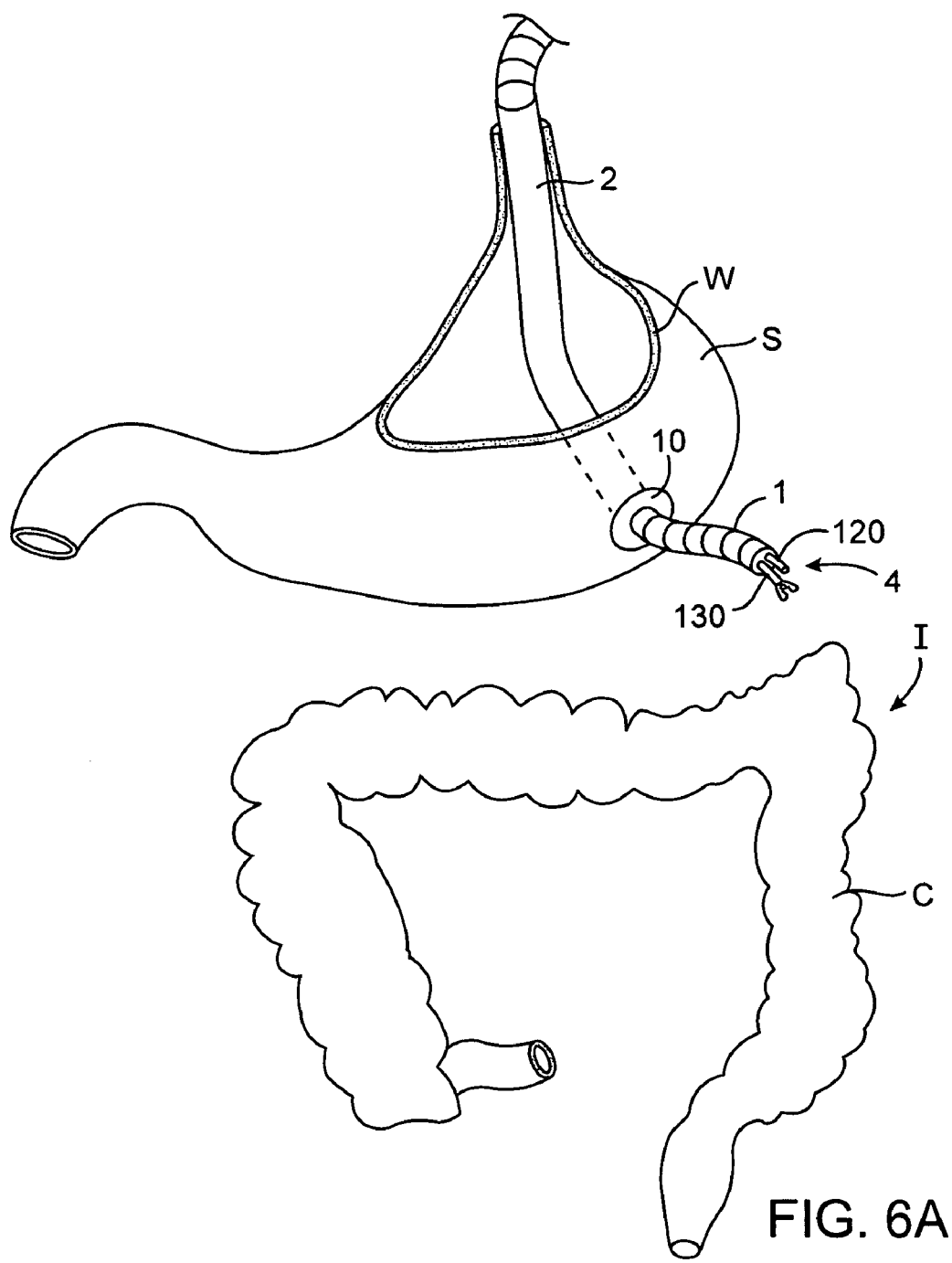
FIGS. 6A-6D are schematic views, partially in section, illustrating a method of performing per-oral, transgastric gastroenterostomy.
Figure 6B:
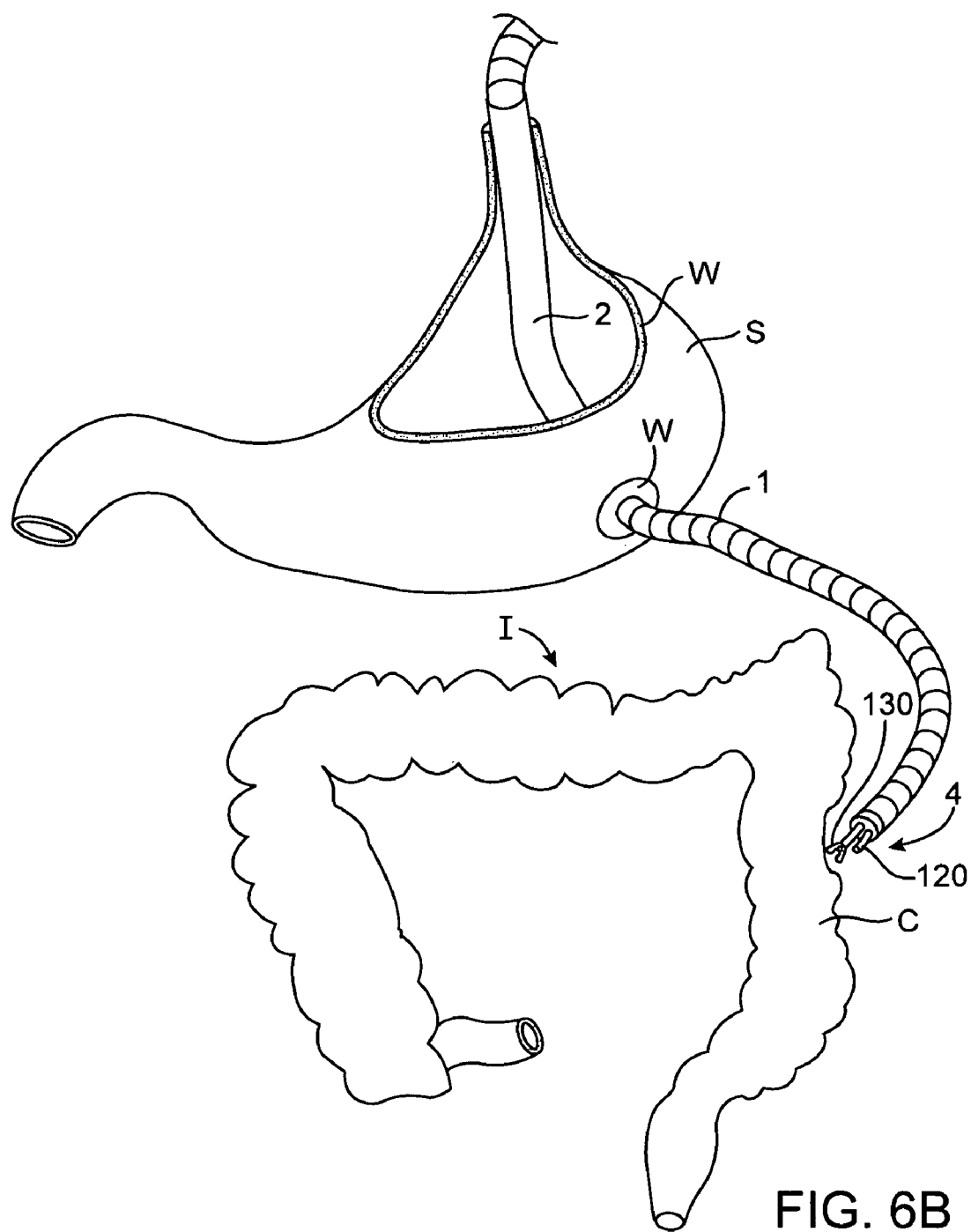

As seen in FIG. 6B, overtube 1 has been steered and/or shape-locked in proximity with a segment of the patient's intestines I. Although the overtube illustratively has been positioned in proximity to the patient's colon C, it should be understood that the overtube alternatively may be positioned in proximity to any alternative portion of the small or large intestine, or any other organ. Overtube 1 illustratively comprises multiple lumens. Tools 4, including endoscope 120 and grasper 130, may be advanced through the lumens, e.g., to provide visualization and engage tissue, respectively.

Figure 6C:
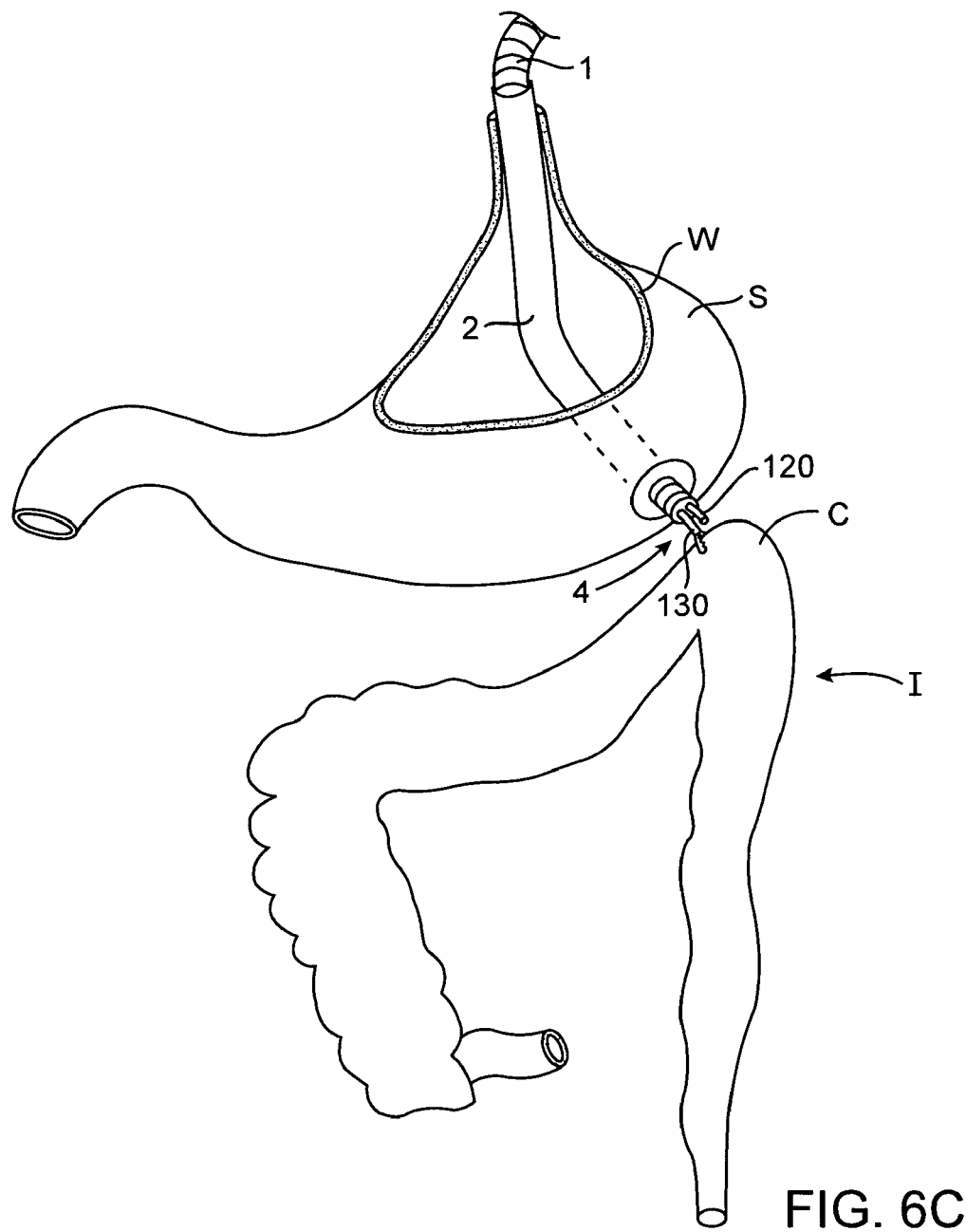

In FIG. 6C, colon C is engaged with grasper 130. With the colon engaged, overtube 1 is retracted back into the GI lumen to approximate the colon and the wall of the patient's stomach. The colon is then secured to the stomach at the position of the breach in the wall of the stomach. Such securement may be achieved, for example, utilizing methods and apparatus described in Applicant's co-pending U.S. patent application Ser. No. 10/865,243, filed Jun. 9, 2004, which is incorporated herein by reference in its entirety.

Figure 6D:
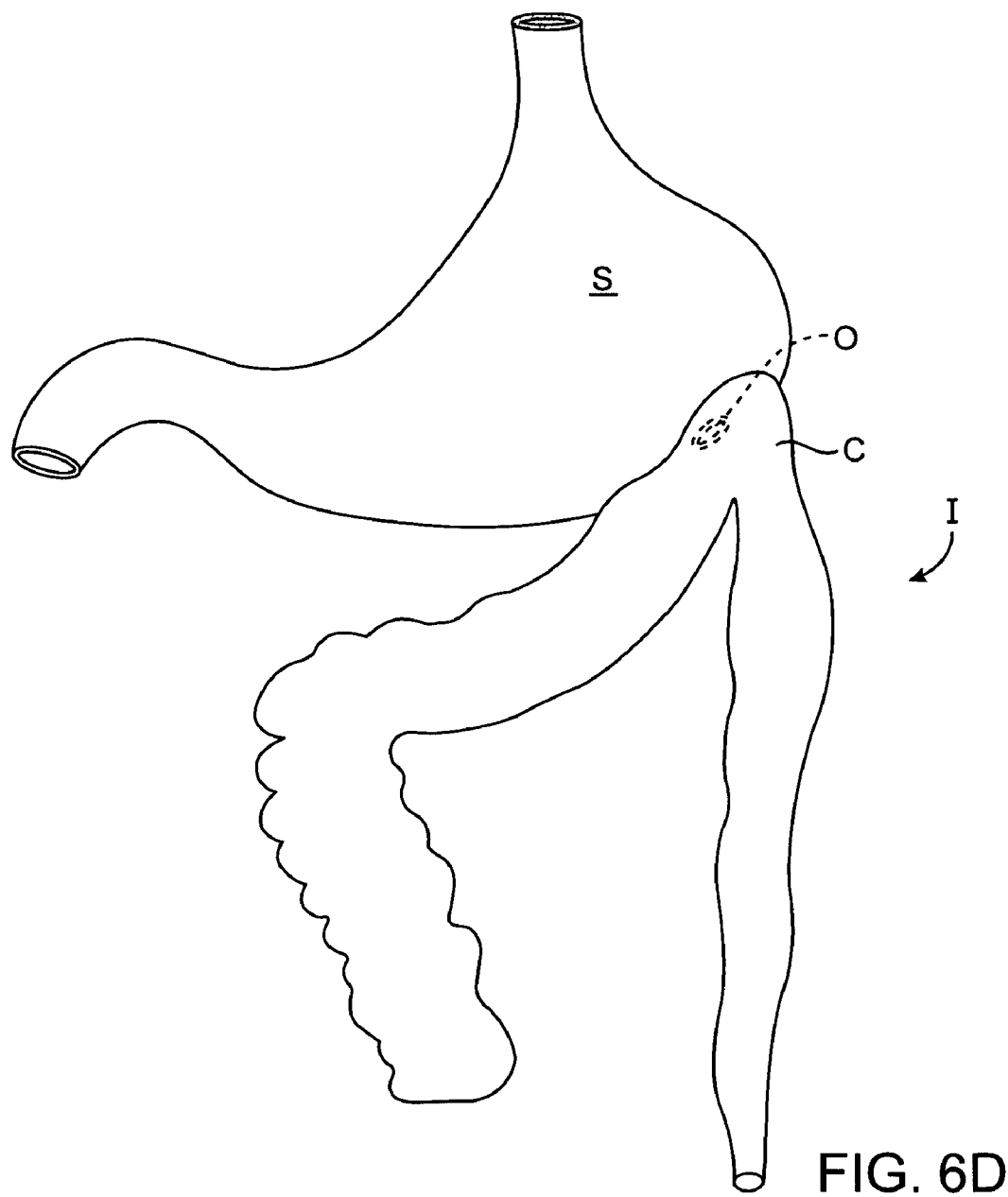

In FIG. 6D, a breach is then formed in the wall of the colon, e.g., via previously described piercing elements, in the vicinity of the securement to the stomach in order to form ostomy O between the stomach and the colon. It is expected that the gastroenterostomy may cause food to bypass at least a portion of the stomach and/or intestines, thereby reducing absorption of the food and treating morbid obesity. Although the gastroenterostomy illustratively has been formed via a per-oral, transgastric procedure, it should be understood that the ostomy alternatively may be formed via a per-anal, transcolonic procedure.

With reference now to FIG. 7, an illustrative method of sealing a breach in the patient's gastrointestinal lumen is described. In FIG. 7A, stomach S illustratively comprises breach B in wall W, for example, at a location through which a transgastric procedure has been conducted. Overtube 1 is positioned within the patient's stomach, and tools 4 comprising endoscope 120 and tissue manipulation instrument 200 have been advanced therethrough.

Instrument 200 is configured to engage, fold and/or secure tissue. The assembly illustratively comprises a catheter or tubular body 212, which may be sufficiently flexible as to facilitate advancement into a body lumen, e.g., transorally, endoluminally, percutaneously, laparoscopically, etc. Tubular body 212 may be configured to be torqueable through various methods, e.g., utilizing a braided tubular construction. Tissue manipulation assembly 214 is located at the distal end of tubular body 212 and is generally used to contact, engage, fold and/or secure tissue.

Tissue manipulation assembly 214 comprises launch tube 218 extending from the distal end of body 212 and in-between the arms of upper extension member or bail 220. Launch tube 218 may define launch tube opening 224 through which needle 225 may be advanced, e.g., for deploying securing elements across engaged tissue. Launch tube 218 may be pivotally connected near or at its distal end via hinge or pivot 222 to the distal end of first bail 220. Second extension member or bail 226 may similarly extend from the distal end of body 212 in a longitudinal direction substantially parallel to first bail 220. First bail 220 and second bail 226 need not be completely parallel so long as an open space between first bail 220 and second bail 226 is sufficiently large to accommodate the drawing of tissue between the two members.

Tissue acquisition member 228 may be an elongate member, e.g., a wire, hypotube, a composite thereof, etc., which terminates at previously described tissue grasper 130. Tissue acquisition member 228 may extend through body 212 and distally between first bail 220 and second bail 226. Acquisition member 228 may also be translatable and actuable relative to body 212 such that tissue grasper 130 is able to translate longitudinally between first bail 220 and second bail 226, and to actuate for engaging tissue.

Figure 7A:
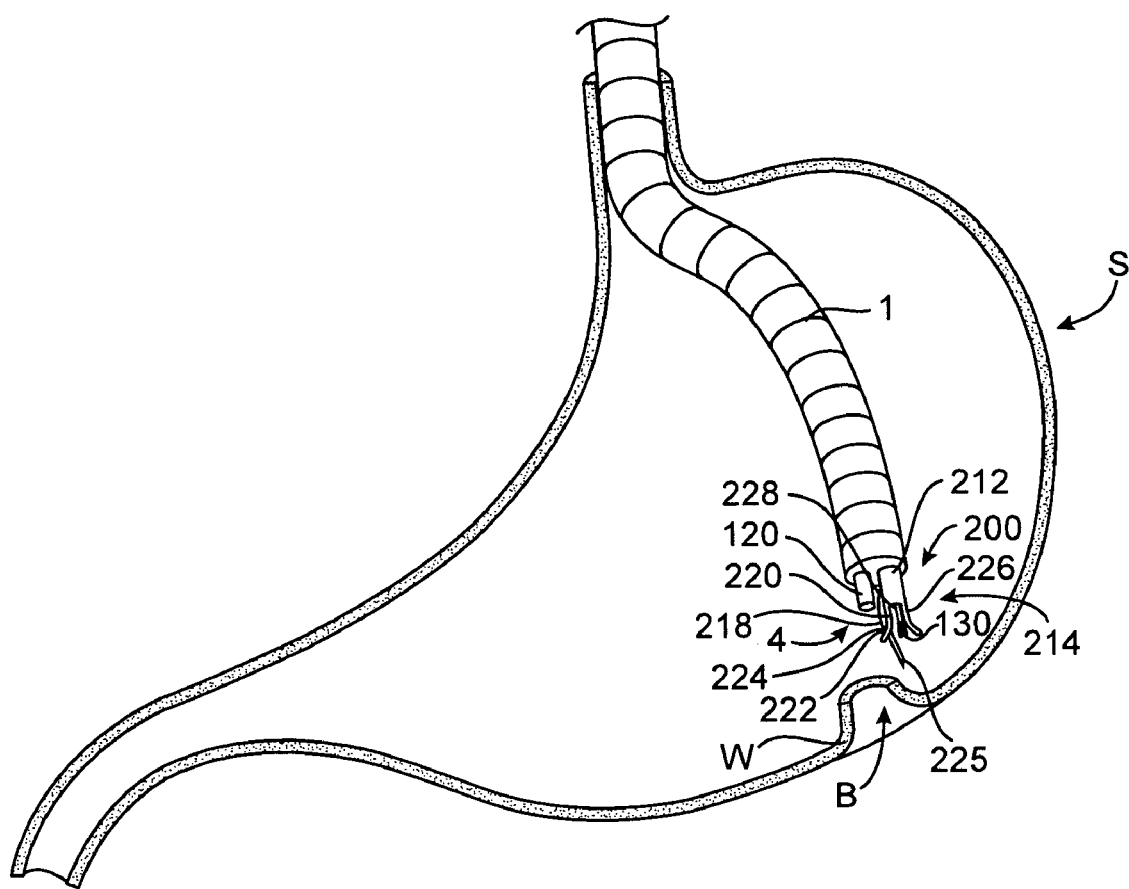
FIGS. 7A-7F are side views, partially in section, as well as a cross-sectional view, illustrating a method of sealing a breach in a patient's gastrointestinal lumen.
Figure 7B:
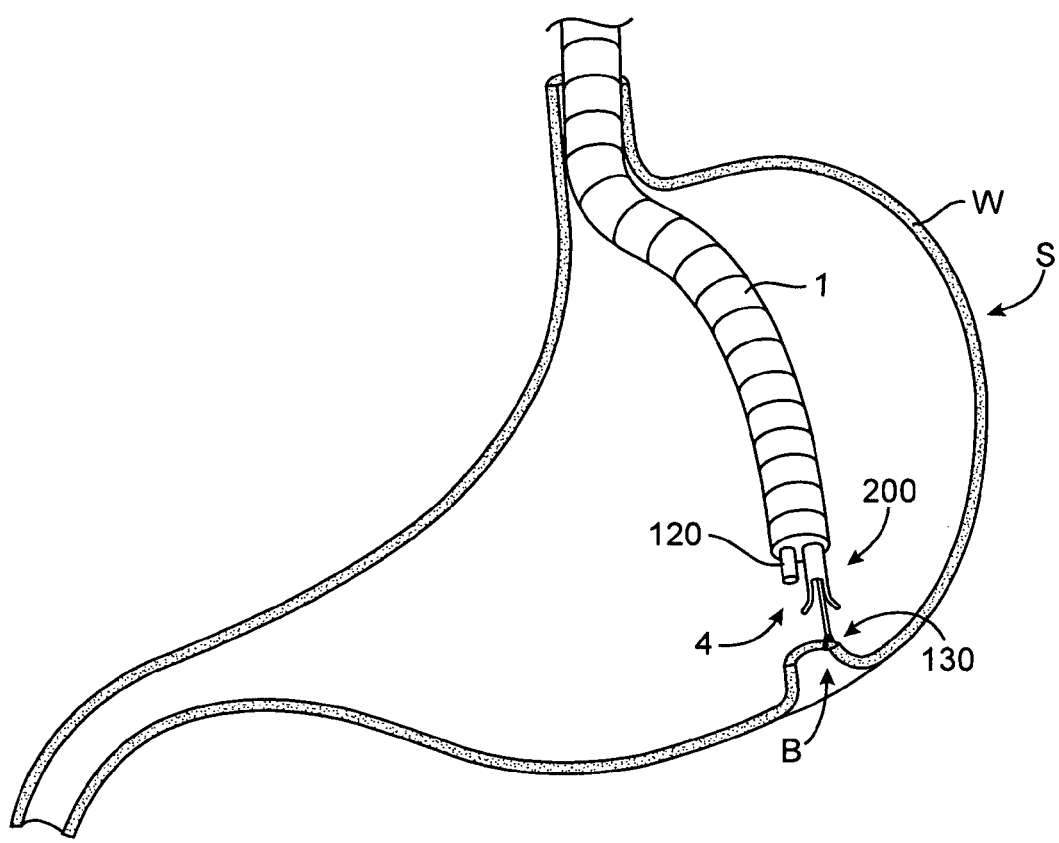
Figure 7C:
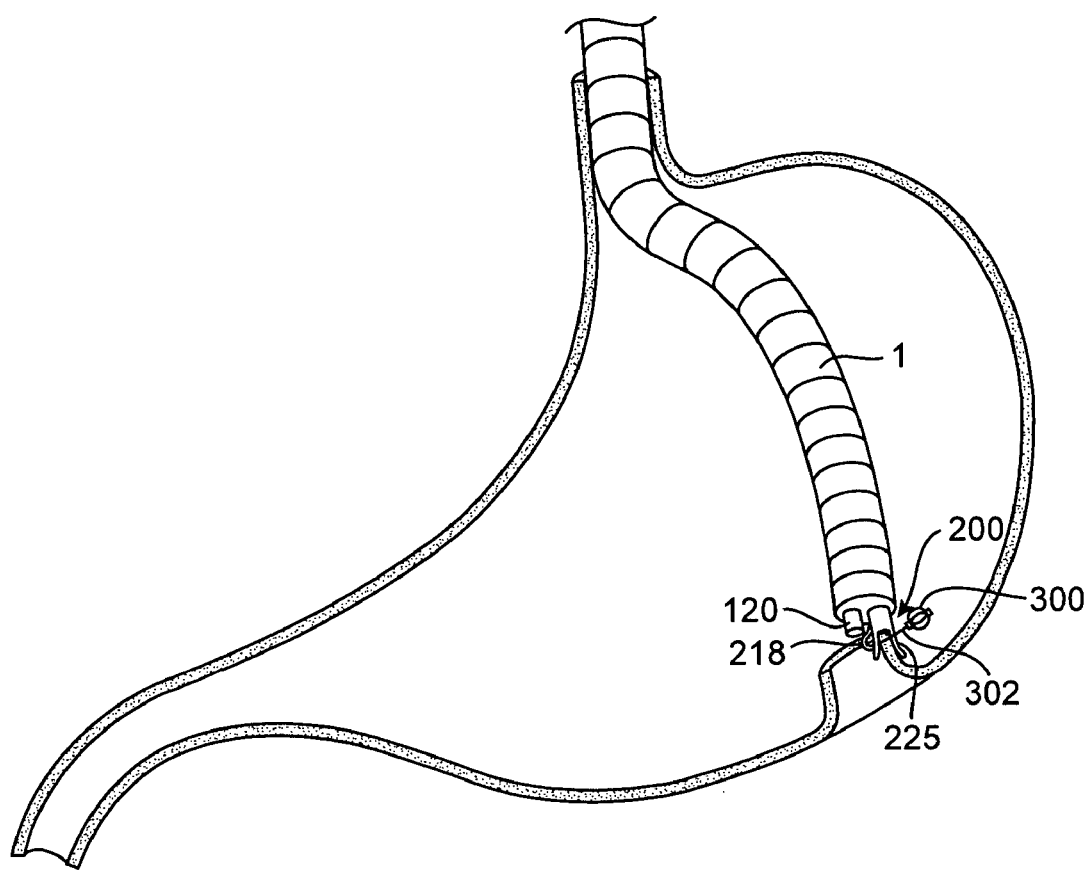

As seen in FIG. 7B, grasper 130 may be extended distally of bails 220 and 226, and may engage tissue at the edge of breach B. The grasper then may be retracted between the bails, such that the tissue edge is disposed therebetween, and launch tube 218 may be actuated to align launch tube opening 224 with the engaged tissue. As seen in FIG. 7C, needle 225 then may be advanced across the tissue, and illustrative tissue anchor 300 may be deployed. Tissue anchors are described in greater detail in Applicant's co-pending U.S. patent application Ser. No. 10/865,243, filed Jun. 9, 2004, which has been incorporated herein by reference.

Figure 7D:
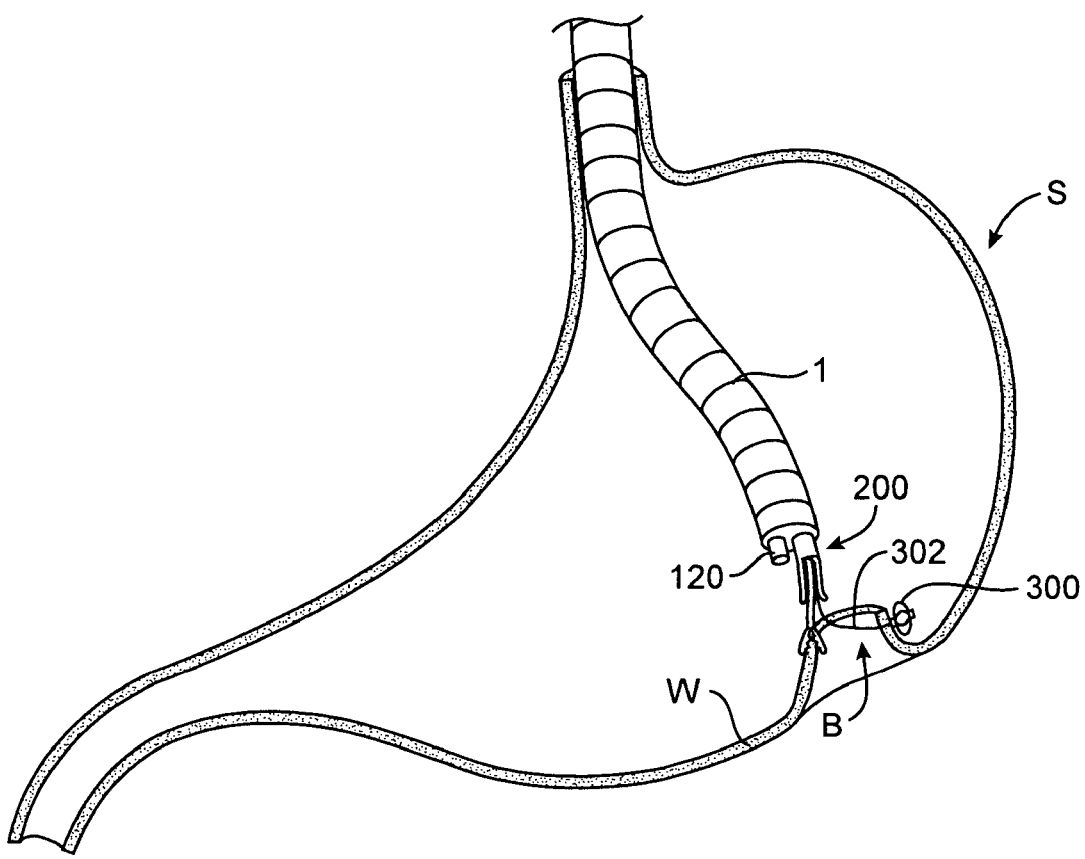
Figure 7E:
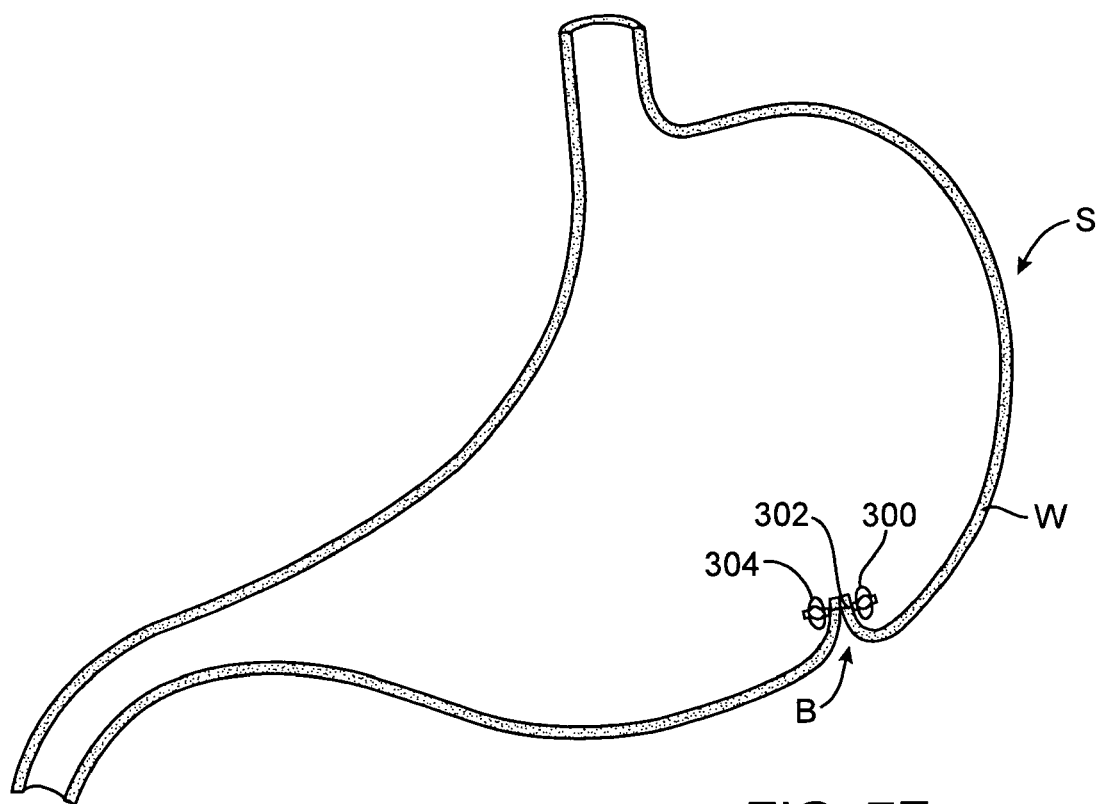

Once anchor 300 has been deployed, needle 225 may be retracted, and grasper 130 may release the engaged tissue. In FIG. 7D, with suture 302 extending from anchor 300, tissue manipulation assembly 214 and grasper 130 may engage an opposing tissue edge of breach B, and the process may be repeated. As seen in FIG. 7E, tissue anchor 304, which is coupled to anchor 300 via suture 302, may be positioned on the opposing side of the breach, and the tissue anchors may be cinched together, e.g., by shortening a length of suture disposed therebetween. This approximates the opposing edges of breach B in order to seal the breach.

Figure 7F:
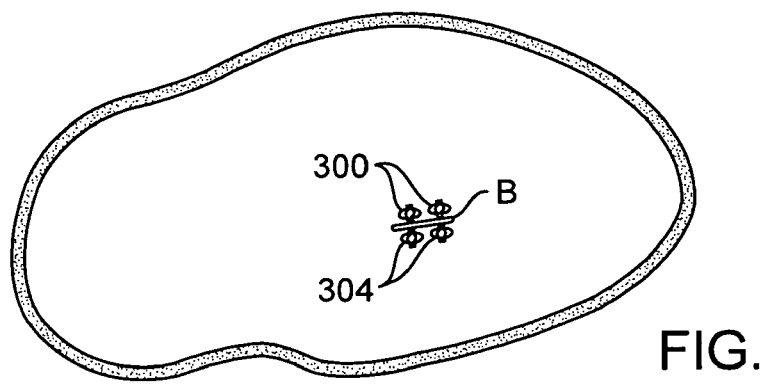

As seen in the cross-sectional view of FIG. 7F, when breach B is of substantial size, it may be desirable to place multiple sets of tissue anchors across the edges of the breach, e.g., in different planes of the breach. Two sets of anchors 300/304 are illustratively shown, but it should be understood that any alternative number of anchor sets may be provided.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. A method for performing a surgical procedure, the method comprising:
   endoluminally advancing a conduit per-orally into a patient's stomach;
   breaching a wall of the stomach;
   securing the conduit to the wall in a vicinity of the breach;
   rigidizing the conduit;
   advancing an instrument along or through the conduit such that the instrument passes transluminally from the interior to the exterior of the stomach;
   performing the surgical procedure with the instrument;
   retrieving the instrument back into the stomach;
   grasping a first portion of tissue on the wall of the stomach at or near the location of the breach;
   advancing a needle through the first portion of tissue;
   deploying a first anchor from the needle;
   retracting the needle from the first portion of tissue, whereby a suture extends from the first anchor and through the first portion of tissue;
   releasing the first portion of tissue;
   grasping a second portion of tissue on the wall of the stomach at or near the location of the breach;
   advancing the needle through the second portion of tissue;
   deploying a second anchor from the needle, the second anchor being disposed on the suture;
   retracting the needle from the second portion of tissue, whereby the suture extends from the second anchor and through the second portion of tissue; and
   releasing the second portion of tissue.

2. The method of claim 1, wherein endoluminally advancing a conduit further comprises advancing an overtube conduit having a lumen, the instrument advanced through the lumen.

3. The method of claim 1, wherein breaching a wall of the stomach further comprises breaching the wall with a distal region of the conduit.

4. The method of claim 1, wherein breaching a wall of the stomach further comprises breaching the wall with the instrument.

5. The method of claim 1, wherein breaching a wall of the stomach further comprises breaching the wall with a piercing element.

6. The method of claim 1, wherein securing the conduit to the wall further comprises securing the conduit with first and second members, the first member disposed on an interior surface of the wall, the second member disposed on an exterior surface of the wall.

7. The method of claim 6, wherein securing the conduit with first and second members further comprises securing the conduit with first and second balloon members.

8. The method of claim 1, wherein rigidizing the conduit further comprises shape-locking the conduit.

9. The method of claim 1, wherein advancing an instrument further comprises advancing a guide along or through the conduit such that the guide transluminally passes from the interior to the exterior of the stomach, then advancing the instrument along or through the guide.

10. The method of claim 9 further comprising steering the guide.

11. The method of claim 9 further comprising shape-locking the guide.

12. The method of claim 1, wherein performing the procedure comprises performing a diagnostic procedure.

13. The method of claim 1, wherein performing the procedure comprises performing a therapeutic procedure.

14. The method of claim 1, wherein performing the procedure further comprises performing a gastroenterostomy procedure.

15. The method of claim 1, wherein endoluminally advancing a conduit into a patient's stomach further comprises advancing the conduit transluminally out of the stomach.

16. The method of claim 1, wherein the first anchor is coupled to the second anchor via the suture when the first anchor is deployed from the needle.

17. The method of claim 1, wherein the step of grasping a first portion of tissue comprises grasping the first portion of tissue using a grasping member that is movable independently of the needle.

18. The method of claim 17, wherein the step of grasping a second portion of tissue comprises grasping the second portion of tissue using the grasping member.

19. A method for performing a diagnostic or therapeutic medical procedure on a patient, the method comprising:
endoluminally advancing a conduit per-orally into a stomach of the patient;
breaching a wall of the stomach;
rigidizing the conduit;
advancing an instrument along or through the conduit such that the instrument passes transluminally from the interior to the exterior of the stomach;
performing the medical procedure with the instrument;
retrieving the instrument back into the stomach;
grasping a first portion of tissue on the wall of the stomach at or near the location of the breach with a grasping member;
advancing a needle through the first portion of tissue;
deploying a first anchor from the needle;
retracting the needle from the first portion of tissue, whereby a suture extends from the first anchor and through the first portion of tissue; and
releasing the first portion of tissue.

20. The method of claim 19, wherein breaching a wall of the stomach further comprises breaching the wall with the instrument.

21. The method of claim 19, wherein breaching a wall of the stomach further comprises breaching the wall with a piercing element.

22. The method of claim 19, wherein advancing an instrument further comprises advancing a guide along or through the conduit such that the guide transluminally passes from the interior to the exterior of the stomach, then advancing the instrument along or through the guide.

23. The method of claim 19, wherein the grasping member is movable independently of the needle.

24. A method for performing a diagnostic or therapeutic medical procedure on a patient, the method comprising:
endoluminally advancing a conduit into a stomach of the patient;
piercing a wall of the stomach to create a breach in the wall;
rigidizing the conduit;
advancing an instrument along or through the conduit such that the instrument passes transluminally through the breach in the wall of the stomach;
performing the medical procedure with the instrument;
retrieving the instrument back into the stomach;
grasping a first portion of tissue on the wall of the stomach at or near the location of the breach with a grasping member;
advancing a needle through the first portion of tissue;
deploying a first anchor from the needle;
retracting the needle from the first portion of tissue, whereby a suture extends from the first anchor and through the first portion of tissue; and
releasing the first portion of tissue.

25. The method of claim 24, further comprising:
grasping a second portion of tissue on the wall of the stomach at or near the location of the breach and opposed from the first portion of tissue with the grasping member;
advancing the needle through the second portion of tissue;
deploying a second anchor from the needle, the second anchor being attached to the first anchor by the suture;
retracting the needle from the second portion of tissue, whereby the suture extends from the second anchor and through the second portion of tissue; and
releasing the second portion of tissue.

26. The method of claim 25, further comprising:
shortening a length of the suture disposed between the first and second anchors.

27. The method of claim 26, further comprising:
deploying a third anchor and fourth anchor joined by a suture through tissue on the wall of the stomach at or near the location of the breach.

28. The method of claim 25, wherein the first anchor is attached to the second anchor via the suture when the first anchor is deployed from the needle.

29. The method of claim 25, wherein the step of grasping a first portion of tissue comprises grasping the first portion of tissue using the grasping member that is movable independently of the needle, and wherein the step of grasping a second portion of tissue comprises grasping the second portion of tissue using the grasping member.

30. The method of claim 24, wherein the grasping member is movable independently of the needle.

* * * * *